(12) United States Patent
Steinebach

(10) Patent No.: US 10,234,471 B2
(45) Date of Patent: Mar. 19, 2019

(54) METHOD FOR DETERMINING THE POSITION OF MEASUREMENT LOCATIONS IN A MEASUREMENT SYSTEM

(71) Applicant: Siemens Healthcare Diagnostics Products GmbH, Marburg (DE)

(72) Inventor: Wolfgang Steinebach, Salz (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 15/134,036

(22) Filed: Apr. 20, 2016

(65) Prior Publication Data

US 2016/0313359 A1 Oct. 27, 2016

(30) Foreign Application Priority Data

Apr. 23, 2015 (EP) ..................... 15164797

(51) Int. Cl.
*G01N 35/02* (2006.01)
*G01N 35/04* (2006.01)
*H03L 7/08* (2006.01)
*G01N 35/00* (2006.01)
*H03L 7/083* (2006.01)

(52) U.S. Cl.
CPC ..... *G01N 35/025* (2013.01); *G01N 35/00732* (2013.01); *G01N 35/04* (2013.01); *H03L 7/08* (2013.01); *H03L 7/083* (2013.01); *G01N 2035/0439* (2013.01); *G01N 2035/0491* (2013.01); *H03L 2207/50* (2013.01)

(58) Field of Classification Search
None
See application file for complete search history.

(56) References Cited

U.S. PATENT DOCUMENTS 4,829,217 A * 5/1989 Kameyama .......... G03G 15/757
  318/37
2010/0309487 A1* 12/2010 Hyoudou ............... G01N 21/07
  356/620

FOREIGN PATENT DOCUMENTS

| DE | 43 13 399 | 10/1993 |
| EP | 1 493 012 | 1/2005 |
| EP | 2 309 251 | 4/2011 |
| WO | WO 03/087779 | 10/2003 |
| WO | WO 2009/094761 | 8/2009 |

OTHER PUBLICATIONS

European Search Report of European Application No. 15164797.1-1553 dated Oct. 5, 2015.

* cited by examiner

*Primary Examiner* — Kathryn Wright
(74) *Attorney, Agent, or Firm* — Dugan & Dugan, PC

(57) ABSTRACT

The present invention relates to a method for determining the position of a multiplicity of measurement locations in a measurement system of an automated analysis device, and a corresponding automated analysis device with an integrated circuit, which is configured as phase locked loop.

16 Claims, 3 Drawing Sheets

METHOD FOR DETERMINING THE POSITION OF MEASUREMENT LOCATIONS IN A MEASUREMENT SYSTEM

CROSS REFERENCE TO RELATED APPLICATION

This claims priority to European Patent Application No. EP 15164797.1, filed Apr. 23, 2015, which is hereby incorporated by reference herein in its entirety for all purposes.

FIELD

The present invention lies in the field of automated analysis devices, in particular for in-vitro diagnostics, and it relates to a method for determining the position of a multiplicity of measuring locations in a measurement system of an analysis device and to an automated analysis device with a controller for such a method.

BACKGROUND

Current analysis devices, as are routinely used in analytics, forensics, microbiology and clinical diagnostics, are able to carry out a multiplicity of detection reactions and analyses with a sample. In order to be able to carry out a multiplicity of examinations in an automated manner, various automatically operating apparatuses for the spatial transfer of measurement cells, reaction containers and reagent containers are required, such as, e.g., transfer arms with gripper functions, transport belts or rotatable transport wheels, as well as apparatuses for transferring liquids, such as, e.g., pipetting apparatuses. The devices comprise a central control unit which, by means of appropriate software, is able to largely autonomously plan and work through the work steps for the desired analyses.

Many of the analysis methods used in such autonomously operating analysis devices are based on optical methods. Determining clinically relevant parameters, such as, e.g., the concentration or activity of an analyte, is often carried out by virtue of part of a sample being mixed with one or more test reagents in a reaction vessel, which may also be the measurement cell, as a result of which a biochemical reaction or a specific binding reaction, e.g., an antigen/antibody binding reaction, are started, which brings about a measurable change in an optical, or other, physical property of the test set-up.

In addition to spectrophotometry and turbidimetry, nephelometry is a widely used analysis method. Corresponding analysis devices therefore have corresponding photometric measurement apparatuses.

A photometric measurement apparatus comprises at least one light source and at least one photodetector. Typically, the arrangement of light source and photodetector is selected in such a way that the light emitted by the light source passes through a measurement cell arranged at a recording location and the light detector measures the light which leaves the measurement cell again.

Analysis devices in which the photometric measurement apparatus is moveable relative to the measurement cells or in which the measurement cells are moveable relative to the photometric measurement apparatus are finding increasing use. This is advantageous in that a measurement apparatus is able, as it were, to examine a multiplicity of samples simultaneously, which significantly increases the sample throughput.

EP-A1-2309251 describes an apparatus for the photometric examination of samples, in which a multiplicity of stationary measurement locations are arranged on a circular trajectory at a circular apparatus for receiving reaction vessels, while the photometric measurement apparatus is moveable on a horizontal trajectory about the vertical axis of the apparatus for receiving reaction vessels. Naturally, it is alternatively also possible for the photometric measurement apparatus to have a stationary embodiment and for the apparatus for receiving reaction vessels to be rotated about the vertical axis thereof.

In such photometric systems, in which the photometric measurement apparatus is moved relative to the measurement cell (or vice versa), at least one measured value is detected per revolution for each one of the measurement locations. What must be ensured here for the correct measured value detection is that each measurement location is fixed during each revolution and retrieved by the photometric measurement apparatus. To this end, the system comprises a physical reference location as a reference point, which defines an initial position for the relative movement between measurement apparatus and measurement locations. Then, the individual measurement locations are determined in the case of a known, constant rotational speed by virtue of measuring time intervals relative to the physical reference location. The measured time intervals can then be associated with specific measurement locations. By way of example, a physical reference location can be formed by a fork light barrier, which is passed through once during each revolution.

However, the accuracy of the determination of the physical reference location is restricted in practice by various factors, such as, e.g., interference or noise in the photoelectric sensor signal or an insufficiently homogeneous movement of the measurement apparatus or of the measurement locations, as occurs often, in particular, in the case of an actuation by stepper motors. An inaccurate determination of the physical reference location leads to an inaccurate determination of the measurement locations in the subsequent revolution, which in turn, as a consequence, results in a reduced accuracy of the measured value detection. This, in turn, can lead to completely invalid faulty measurements, which reduces the throughput of the measurement system.

SUMMARY

Therefore, it is an object of the invention to improve a measurement system for an automated analysis device, of the type set forth at the outset, in such a way that an accurate measured value detection is ensured.

According to the invention, the object is achieved by virtue of providing a method which enables a more accurate determination of the position of the measurement locations in the measurement system by virtue of the position of a virtual reference location being determined by means of a phase locked loop, proceeding from the determined position of the physical reference location.

It was determined that the method according to the invention reduces the number of incorrect measurements which can be traced back to location errors.

Therefore, the subject matter of the present invention is a method for determining the position of a multiplicity of measurement locations in a measurement system, wherein the measurement system comprises a) a circular apparatus for receiving reaction vessels, which has a multiplicity of measurement locations arranged on a circular trajectory and a physical reference location, and b) a measurement apparatus, and wherein either the apparatus for receiving reaction vessels is rotatable about the vertical axis thereof or the measurement apparatus is moveable on a horizontal circular trajectory about the vertical axis of the apparatus for receiving reaction vessels. The method comprises the following steps:

i. rotating the apparatus for receiving reaction vessels about the vertical axis thereof or moving the measurement apparatus on a horizontal circular trajectory about the vertical axis of the apparatus for receiving reaction vessels with a constant rotational speed in each case;

ii. measuring a physical reference signal at the physical reference location during each revolution;

iii. determining a virtual reference location by means of a phase locked loop and iv. calculating the position of the measurement locations on the basis of the virtual reference location.

The physical reference location is preferably formed by an optoelectronic sensor system, such as, for example, a disposable photoelectric sensor apparatus, e.g., in the form of a fork light barrier. To this end, a light source and a photodetector are arranged opposite to one another on the measurement apparatus, while a stop is provided at a position on the apparatus for receiving reaction vessels, which stop is able to interrupt the light signal falling on the photodetector from the light source. The position at which the stop is arranged defines the physical reference location. Accordingly, the physical reference signal consists of an interrupted light signal in this case, which is generated by a photoelectric sensor at the physical reference location.

Alternatively, the physical reference location is also definable by other sensor systems, e.g., by Hall sensor systems or capacitive sensor systems.

According to the invention, the physical reference signal at the physical reference location is recorded during each revolution of the apparatus for receiving reaction vessels about the vertical axis thereof or during each revolution of the measurement apparatus on a horizontal circular trajectory about the vertical axis of the device for receiving reaction vessels, and a virtual reference location is determined by means of a phase locked loop. A phase locked loop (PLL) is an electronic circuit arrangement, which comprises a feedback control loop and, in general, serves to set a stable phase angle of a location over the course of a periodic procedure.

A phase locked loop suitable for determining a virtual reference location according to the invention comprises at least a phase detector, a loop filter such as, e.g., a low-pass filter, and a pulse generator.

In principle, a distinction is made between an unlocked state of the phase locked loop ("unlocked PLL") and a locked state of the phase locked loop ("locked PLL"). When the measurement system is put into operation, the phase angle between pulse sequence of the actually measured physical reference signals and a pulse signal sequence generated by the pulse generator is still unknown, i.e., the phase locked loop is in the unlocked state. The phase locked loop is only in the locked state once the pulse generator generates a corrected pulse signal sequence and forwards the latter to the phase detector, the phase deviation of which pulse signal sequence drops below a defined minimum phase deviation.

Preferably, the phase locked loop is configured in such a way that the phase detector, in the locked state, establishes the deviation of the last-measured physical reference signal from the phase of a pulse signal sequence generated by the pulse generator and forwards the latter to the loop filter.

The loop filter then forwards the deviation of the last-measured phase of the physical reference signals from the phase of the pulse signal sequence generated by the pulse generator to the pulse generator, together with a predetermined correction factor. Furthermore, the loop filter establishes the mean value over N measured periods of the physical reference signals and likewise forwards this to the pulse generator.

Preferably, the loop filter continuously adapts the mean value over N measured periods of the physical reference signals with each revolution.

In the locked state, the pulse generator then generates a pulse signal sequence, the periods of which correspond to the mean value over N measured periods of the physical reference signals and in which the phase angle of the pulses is corrected by the correction factor in such a way that the deviation from the mean phase angle of the last-measured phases of the physical reference signals is minimal. This pulse signal sequence is then, firstly, returned to the phase detector for closed-loop control purposes and, secondly, output as output pulse sequence. Each pulse of the output pulse sequence then corresponds to the virtual reference location of the associated revolution.

The correction factor corresponds to the gain or the damping, with which the phase locked loop undertakes a phase correction. The correction factor should be established empirically for each given system by way of simulation experiments. Alternatively, the correction factor can also be calculated with the aid of a mathematical model or it can be established in a trial setup.

Preferably, the phase locked loop is furthermore configured in such a way that the phase detector initially measures the period between a first and a second physical reference signal and forwards this to the pulse generator during the startup of the measurement system, i.e., while it is still in the unlocked state.

The pulse generator forwards the physical reference signals to the phase detector in the still unlocked state.

Thereupon, the phase detector establishes the deviation of the last-measured physical reference signal from the phase of the pulse signal sequence generated by the pulse generator. The phase locked loop is switched into the locked state if the deviation then is smaller than a predetermined threshold. The threshold should be established empirically for each given system by way of simulation experiments. Alternatively, the threshold can also be calculated with the aid of a mathematical model or it can be established in a trial setup.

Preferably, the condition that the deviation is less than a predetermined threshold must be satisfied at least over a number of two or more ($n \geq 2$) successive revolutions.

Further subject matter of the present invention relates to an automated analysis device with a measurement system, said measurement system comprising a) a circular apparatus for receiving reaction vessels, which has a multiplicity of measurement locations arranged on a circular trajectory and a physical reference location, and b) a measurement apparatus, and wherein either the apparatus for receiving reaction vessels is rotatable about the vertical axis thereof or the measurement apparatus is moveable on a horizontal circular trajectory about the vertical axis of the apparatus for receiving reaction vessels. The analysis device according to the invention furthermore has a control unit and an integrated circuit, wherein the control unit is configured in such a way that it controls a method comprising the following steps:

i. rotating the apparatus for receiving reaction vessels about the vertical axis thereof or moving the measurement apparatus on a horizontal circular trajectory about the vertical axis of the apparatus for receiving reaction vessels with a constant rotational speed in each case;

ii. measuring a physical reference signal at the physical reference location during each revolution;

iii. determining the position of the multiplicity of measurement locations in the measurement system on the basis of a virtual reference location.

The integrated circuit is configured as a phase locked loop, which determines the virtual reference location. Preferably, the integrated circuit is a digital integrated circuit. Particularly preferably, use is made of a field-programmable gate array (FPGA) as digital integrated circuit.

In a preferred analysis device, the measurement system comprises a photometric measurement apparatus. A photometric measurement apparatus can have one or more spectrophotometric apparatuses and/or one or more nephelometric apparatuses. A preferred measurement system is described in EP-A1-2309251.

Preferably, the physical reference location at the circular apparatus for receiving reaction vessels is formed from a photoelectric sensor apparatus. To this end, e.g., a stop is provided at a position on the apparatus for receiving reaction vessels, said stop being able to interrupt a light signal from a light source, which is applied to the measurement apparatus, incident on a photodetector, which is likewise applied to the measurement apparatus. The position at which the stop is arranged defines the physical reference location.

BRIEF DESCRIPTION OF THE DRAWINGS

Persons skilled in the art will understand that the drawings, described below, are for illustrative purposes only. The drawings are not necessarily drawn to scale and are not intended to limit the scope of this disclosure in any way.

Parts which are the same are provided with the same references in all the figures.

DETAILED DESCRIPTION

EXAMPLE

Figure 1:
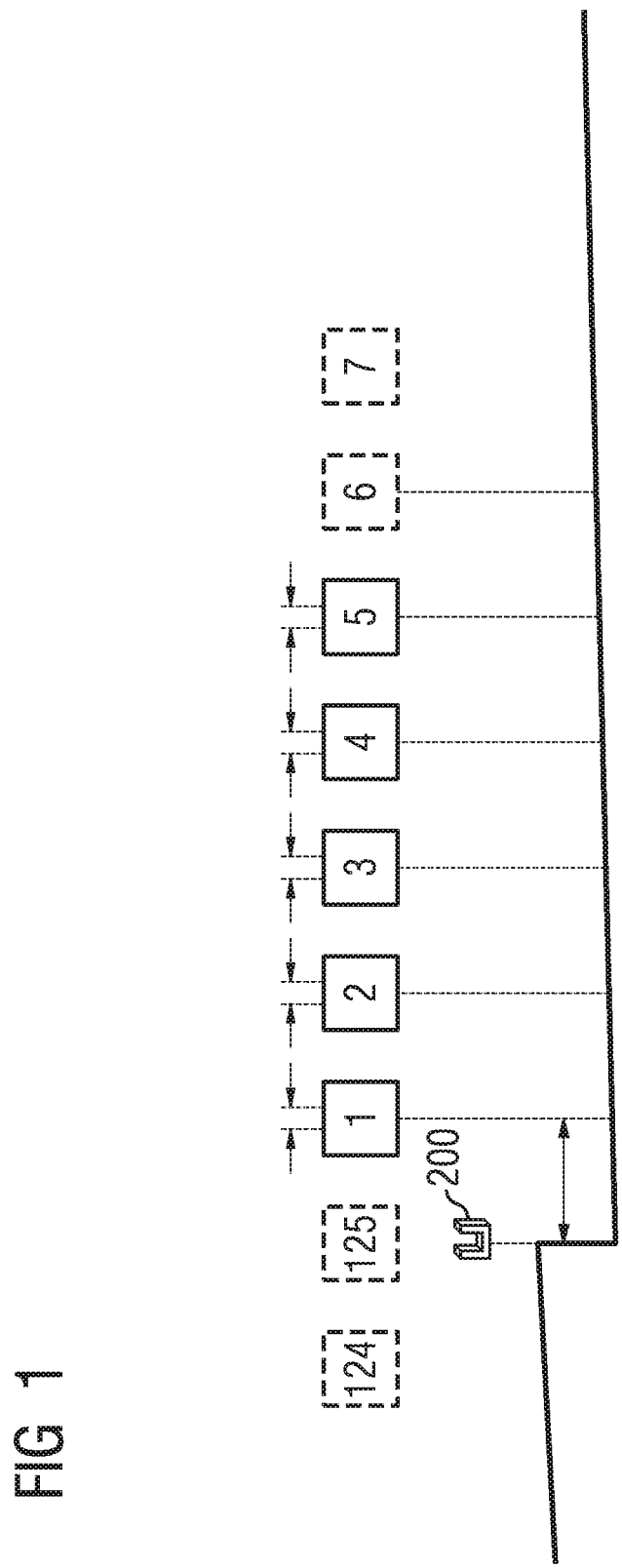
FIG. 1 schematically shows the measurement data detection and location calculation in a measurement system with a photometer rotating about a stationary sample receiving plate.
Figure 2:
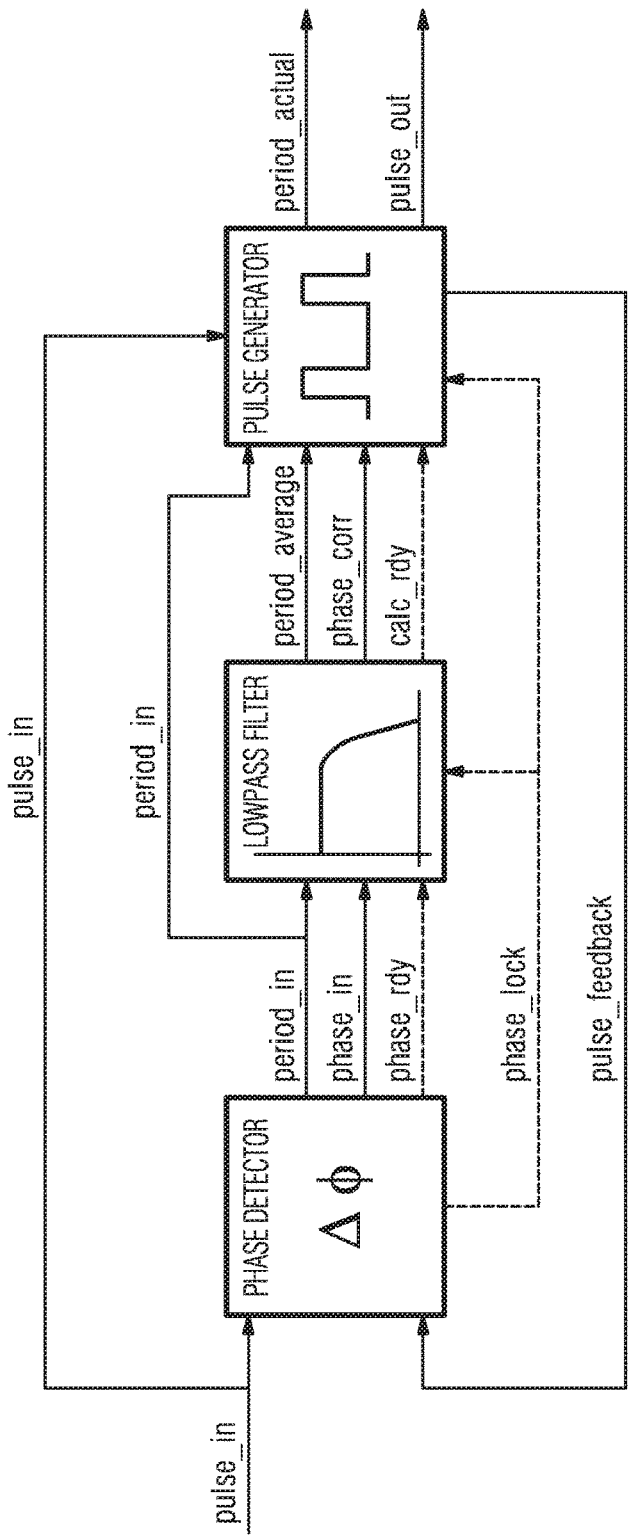
FIG. 2 schematically shows the phase locked loop for reducing the phase noise when determining the position of the measurement locations in a measurement system in accordance with FIG. 1.
Figure 3:
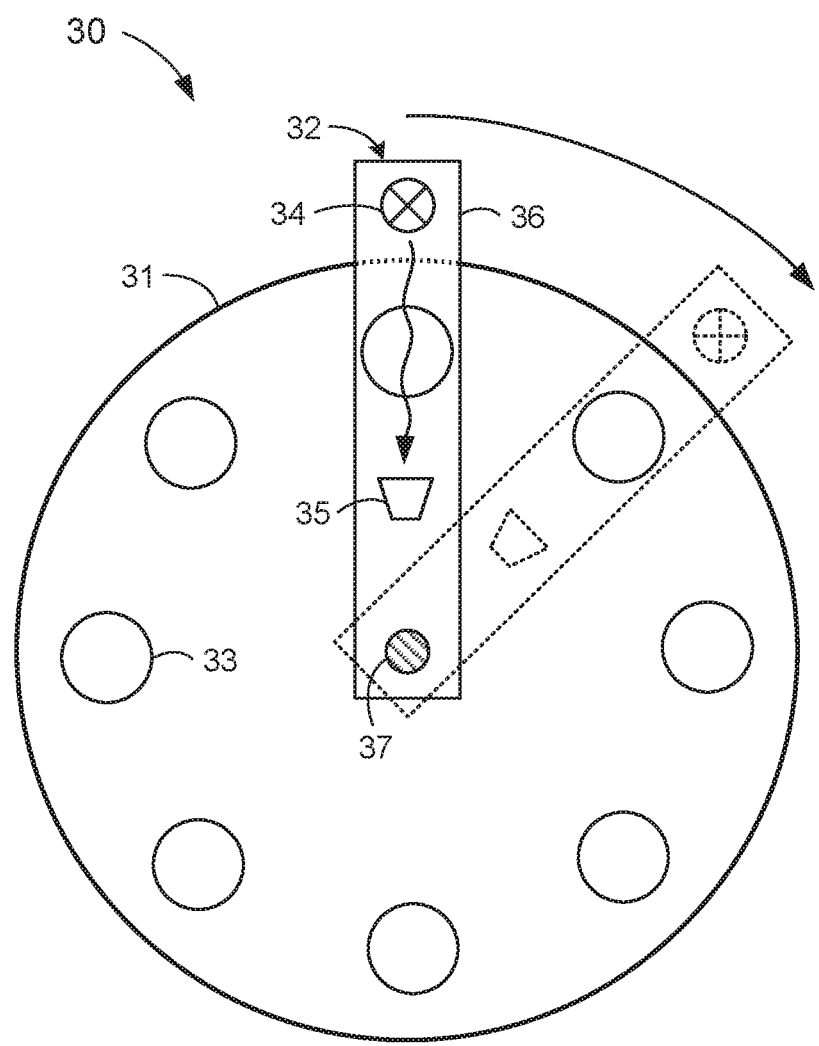
FIG. 3 schematically shows a measurement system in accordance with FIG. 1, wherein measurement system 30 includes a circular cuvette receptacle 31 and a measurement apparatus 32 (e.g., a photometer). Circular cuvette receptacle 31 may have eight receiving positions 33 for holding sample vessels, wherein each receiving position 33 has a respective measurement location situated within. Measurement apparatus 32 may include a light source 34, a photodetector 35, and a movable apparatus 36 that is rotatable about a vertical axis 37.

FIGS. 1 and 2 are used to explain an automated analysis device (not depicted in any more detail here), which comprises a measurement system in which a photometer circles around a circular ring-shaped sample plate for receiving 125 cylindrical reaction vessels with a constant speed (2 Hz).

FIG. 1 schematically shows some of the 125 available receiving positions (i.e., 1-7, 124, and 125) past which the photometer is guided. The physical reference location is formed from a stop for a fork light barrier (200) and it defines the reference point or the initial position, from which the measurement locations 1-125 are arranged at known distances. The known distance between the physical reference location and the first measurement location is indicated by a double-headed arrow. The measurement locations are situated within the receiving locations for the reaction vessels such that an optical property of a reaction preparation in a reaction vessel, which was introduced into the sample plate, can be measured.

For the purposes of correctly detecting measured values, it is necessary to ensure that each measurement location is correctly retrieved during each revolution. In the case of a known, constant rotational speed, the individual measurement locations are determined by measuring time intervals relative to the physical reference location. The measured time intervals can then be associated with the measurement locations.

However, the accuracy of determining the physical reference location is restricted by various factors, such as, e.g., interference or noise in the photoelectric sensor signal or an insufficiently homogeneous movement of the photometer. Determining the physical reference location imprecisely leads to an imprecise determination of the measurement locations in the subsequent revolution, which in turn has a reduced accuracy of the measured value detection as a consequence. This in turn can lead to completely invalid faulty measurements, reducing the throughput of the measurement system.

In order to reduce such erroneous measurements, the automated analysis device described here has a digital integrated circuit in the form of an FPGA, the partial function of which is configured as a phase locked loop which determines a virtual reference location.

FIG. 2 schematically shows the design of the phase locked loop, which was realized by programming an FPGA. Controlling elements are depicted by dashed lines.

Information-containing elements are depicted by full lines.

The input signal (pulse_in) for this arrangement is the physical reference signal, which is generated by the fork light barrier whenever the photometer passes the physical reference location of the measurement system.

When the measurement system is started up, i.e., when it is in the unlocked state, the phase detector (PHASE DETECTOR, $\Delta\Phi$) initially establishes the time interval, i.e., the period, between a first and a second physical reference signal by way of a counter, and the result (period_in) is provided to the loop filter (LOWPASS FILTER) for further processing. Later, in the locked state of the phase locked loop ("locked PLL"), the current phase deviation of the last physical reference signal from the pulse signal sequence (pulse_feedback) generated by the pulse generator (PULSE GENERATOR) is established, and this result (phase_in) is also provided to the loop filter for further processing. The completion of the phase comparison and the establishment of the period duration (period_in) in the phase detector are signaled by the control signal phase_rdy.

The loop filter calculates a mean value over N measured periods (period_average) of the physical reference signals in order thus to establish a mean period value and forward this to the pulse generator. Furthermore, the loop filter forwards the current phase deviation multiplied by a predetermined correction factor (phase_corr) to the pulse generator. The completion of the mean value establishment over N measured periods in the loop filter is signaled by the control signal calc_rdy.

The correction factor corresponds to the gain (or damping) with which the phase locked loop subsequently undertakes a phase correction. Small correction factors bring about a sluggish system, in which the difference in the phase angle from the output pulse (pulse_out) to the input pulse (pulse_in) is only corrected slowly to zero. Here, the filter effect is high, i.e., the deflection of the individual pulses is small in terms of the temporal position thereof. Large correction factors bring about a faster correction of the phase difference with, at the same time, a lower filter effect and therefore an increased pulse deflection. For the system realized here in practice, the correction factor was determined to be $1/2^6$ (0.015625) on the basis of simulations.

The employed loop filter has the property of dynamically adapting the filter depth, i.e., the filter depth N is continuously adapted as filter result when the measurement system is started up, starting with the result from initially one revolution, an averaged result from two revolutions, etc. In order to keep the switching outlay low when calculating the mean value, the dynamic mean value formation was restricted to $N=2^k$, k=0, 1, . . . 10. As a result, the mean value formation can be carried out by a simple shift operation of the binary value.

The pulse generator generates a pulse signal sequence in the locked state. The period of this pulse signal sequence corresponds to the mean value over N measured periods of the physical reference signals. The phase angle and therefore the exact pulse location likewise emerge from the previous pulse locations. A phase deviation from one revolution leads directly to a phase correction adjustable by way of the correction factor. For the purposes of monitoring the revolution duration, the time interval of the last pulses is forwarded to a superordinate computer (period_actual).

No phase angle between the pulse sequence of the actually measured physical reference signals and a pulse signal sequence generated by the pulse generator is known immediately after the measurement system is started up. Therefore, the first pulses are derived directly from the actually measured physical reference signals (pulse_in) and forwarded to the output of the arrangement (pulse_out) and to the phase detector (pulse_feedback). The control signal phase_lock is switched on, i.e. the arrangement transitions into the locked state ("locked PLL"), after the phase deviations established by the phase detector drop below a predetermined threshold over a number of measurements. As a result, the dynamic filtering of the low-pass filter is activated and the pulse generation in the pulse generator is switched over to the filtered pulse period and the phase correction.

Each pulse of the output pulse sequence (pulse_out) in the locked phase corresponds to the virtual reference location of the associated revolution. The output pulse sequence is forwarded to a superordinate calculation unit, which then determines the position of the measurement locations in the photometric measurement system on the basis of the virtual reference location.

What is claimed is:

1. A method for determining the position of a multiplicity of measurement locations in a measurement system, the measurement system comprising:
  a circular apparatus for receiving reaction vessels, which has a multiplicity of measurement locations arranged on a circular trajectory and a physical reference location, wherein each of the measurement locations is arranged at a known distance from the physical reference location, and
  a measurement apparatus,
  wherein either the apparatus for receiving reaction vessels is rotatable about the vertical axis thereof or the measurement apparatus is moveable on a horizontal circular trajectory about the vertical axis of the apparatus for receiving reaction vessels,
  the method comprising the following steps:
  rotating the apparatus for receiving reaction vessels about the vertical axis thereof or moving the measurement apparatus on a horizontal circular trajectory about the vertical axis of the apparatus for receiving reaction vessels with a constant rotational speed in each case;
  measuring a physical reference signal at the physical reference location during each revolution;
  determining a virtual reference location via a phase locked loop that outputs an output pulse sequence in response to the measuring of only the physical reference signal during each revolution wherein each pulse of the output pulse sequence corresponds to the virtual reference location of an associated revolution, the virtual reference location to be used instead of the physical reference location for calculating the position of the measurement locations; and
  calculating the position of the measurement locations based on time intervals of the output pulse sequence corresponding to the virtual reference location along with at least one of the known distance of each of the measurement locations and the constant rotational speed.

2. The method as claimed in claim 1, wherein the physical reference signal consists of an interrupted light signal, which is generated by a photoelectric sensor at the physical reference location.

3. The method as claimed in claim 1, wherein the phase locked loop for determining the virtual reference location comprises a phase detector, a loop filter and a pulse generator.

4. The method as claimed in claim 3, wherein the phase detector, in the locked state, establishes the deviation of the last-measured physical reference signal from the phase of a pulse signal sequence generated by the pulse generator and forwards this to the loop filter.

5. The method as claimed in claim 4, wherein the loop filter forwards the deviation of the last-measured phase of the physical reference signals from the phase of the pulse signal sequence generated by the pulse generator and a predetermined correction factor to the pulse generator and furthermore establishes the mean value over N measured periods of the physical reference signals and likewise forwards this to the pulse generator.

6. The method as claimed in claim 5, wherein the pulse generator then generates a pulse signal sequence, the periods of which correspond to the mean value over N measured periods of the physical reference signals and in which the phase angle of the pulses is corrected by the correction factor in such a way that the deviation from the mean phase angle of the last-measured phases of the physical reference signals is minimal, and it then, firstly, forwards the pulse signal sequence to the phase detector and, secondly, outputs these as the output pulse sequence.

7. The method as claimed in claim 5, wherein the loop filter adapts the mean value over N measured periods of the physical reference signals continuously with each revolution.

8. The method as claimed in claim 3, wherein the phase detector initially measures the period between a first and a second physical reference signal and forwards this to the pulse generator during the startup of the measurement system, while it is still in the unlocked state.

9. The method as claimed in claim 8, wherein the pulse generator, still in the unlocked state, forwards the physical reference signals to the phase detector.

10. The method as claimed in claim 9, wherein the phase detector establishes the deviation of the last-measured physical reference signal from the phase of the pulse signal sequence generated by the pulse generator and the phase locked loop is then switched over into the locked state when the deviation is less than a predetermined threshold.

11. The method as claimed in claim 10, wherein the condition that the deviation is less than a predetermined threshold is satisfied at least over a number n≥2 of successive revolutions.

12. An automated analysis device having a measurement system, the measurement system comprising
a circular apparatus for receiving reaction vessels, which has a multiplicity of measurement locations arranged on a circular trajectory and a physical reference location, wherein each of the measurement locations is arranged at a known distance from the physical reference location, and
a measurement apparatus,
wherein either the apparatus for receiving reaction vessels is rotatable about a vertical axis thereof or the measurement apparatus is moveable on a horizontal circular trajectory about the vertical axis of the apparatus for receiving reaction vessels, and
wherein the automated analysis device also has a control unit and an integrated circuit, wherein the control unit is configured in such a way that it controls a method comprising the following steps:
rotating the apparatus for receiving reaction vessels about the vertical axis thereof or moving the measurement apparatus on a horizontal circular trajectory about the vertical axis of the apparatus for receiving reaction vessels with a constant rotational speed in each case;
measuring a reference signal at the physical reference location during each rotation;
determining the position of the multiplicity of measurement locations in the measurement system based on the integrated circuit outputting an output pulse sequence in response to the measuring of only the reference signal during each revolution wherein each pulse of the output pulse sequence corresponds to a virtual reference location of an associated revolution, the virtual reference location to be used instead of the physical reference location for calculating the position of the multiplicity of measurement locations, and calculating the position of the multiplicity of measurement locations based on time intervals of the output pulse sequence and at least one of the known distance of each of the measurement locations and the constant rotational speed;
and wherein the integrated circuit is configured as a phase locked loop, which determines the virtual reference location.

13. The automated analysis device as claimed in claim 12, wherein the integrated circuit is a digital integrated circuit.

14. The automated analysis device as claimed in claim 12, wherein the measurement apparatus is a photometric measurement apparatus.

15. The automated analysis device as claimed in claim 12, wherein the physical reference location is formed from a photoelectric sensor apparatus.

16. The automated analysis device as claimed in claim 12, wherein the integrated circuit is a field programmable gate array (FPGA).

* * * * *